(12) United States Patent
Tian et al.

(10) Patent No.: US 11,944,584 B2
(45) Date of Patent: Apr. 2, 2024

(54) HEADACHE THERAPEUTIC INSTRUMENT

(71) Applicant: Dongzhimen Hospital, Beijing University of Chinese Medicine, Beijing (CN)

(72) Inventors: Guihua Tian, Beijing (CN); Jian Li, Beijing (CN)

(73) Assignee: Dongzhimen Hospital, Beijing University of Chinese Medicine, Beijing (CN)

( * ) Notice: Subject to any disclaimer, the term of this patent is extended or adjusted under 35 U.S.C. 154(b) by 922 days.

(21) Appl. No.: 16/964,851

(22) PCT Filed: Jul. 8, 2019

(86) PCT No.: PCT/CN2019/094991
§ 371 (c)(1),
(2) Date: Jul. 24, 2020

(87) PCT Pub. No.: WO2020/057232
PCT Pub. Date: Mar. 26, 2020

(65) Prior Publication Data
US 2021/0059893 A1 Mar. 4, 2021

(30) Foreign Application Priority Data
Sep. 19, 2018 (CN) .......................... 201811091566.4

(51) Int. Cl.
*A61H 7/00* (2006.01)
*A61H 39/04* (2006.01)
*A61M 35/00* (2006.01)

(52) U.S. Cl.
CPC ............. *A61H 7/006* (2013.01); *A61H 39/04* (2013.01); *A61M 35/10* (2019.05);
(Continued)

(58) Field of Classification Search
CPC ....... A61H 39/04; A61H 7/006; A61M 37/00; A61M 35/10; A61M 2210/06;
(Continued)

(56) References Cited

U.S. PATENT DOCUMENTS 3,599,250 A * 8/1971 Colomb ................. A45D 19/00
4/517
3,603,320 A * 9/1971 Scipione ................ A45D 19/14
132/270

(Continued)

FOREIGN PATENT DOCUMENTS

CN 2155859 Y 2/1994
CN 2413688 Y 1/2001
(Continued)

OTHER PUBLICATIONS

Cheng-Lin Huang, English translation of CN 2,155,859 Y, Feb. 16, 1994 (Year: 1994).*

(Continued)

*Primary Examiner* — Tu A Vo
*Assistant Examiner* — Alexander Morales
(74) *Attorney, Agent, or Firm* — Shih IP Law Group, PLLC

(57) ABSTRACT

A headache therapeutic instrument is provided, which includes a wearable frame adapted to fit on a human head, massage and transdermal medicine permeation devices, liquid medicine delivery tubes, a liquid medicine delivery device and a liquid medicine storage box. The wearable frame is provided with at least one acupoint locating hole adapted to correspond to acupoints along the human head. The massage and transdermal medicine permeation devices are mounted on the wearable frame and correspond to the acupoint locating hole. The liquid medicine delivery device delivers medicines in the liquid medicine storage box to the (Continued)

massage and transdermal medicine permeation devices through the liquid medicine delivery tubes. The massage and transdermal medicine permeation devices can conduct medicine permeation and massage on corresponding acupoints.

9 Claims, 2 Drawing Sheets

(52) U.S. Cl.
CPC ............... *A61H 2201/105* (2013.01); *A61H 2201/1215* (2013.01); *A61H 2205/021* (2013.01); *A61M 2205/05* (2013.01); *A61M 2210/06* (2013.01)

(58) Field of Classification Search
CPC ...... A61M 2205/05; A61M 2037/0007; A61M 35/00; A61M 35/003; A61M 35/006; A61M 35/30; A61M 37/0015; A61M 37/0092; A61M 2037/0023; A61M 2037/003; A61M 2037/0038; A61M 2037/0046; A61M 2037/0053; A61M 2037/0061; A61F 2009/0035; A61F 2009/0043; A61F 2009/0052; B67D 2210/00131; B05B 9/085; B05B 7/1413; B05B 7/2464; A42B 3/14; A42B 3/30–306; A42B 3/0406; A42B 3/042; A42B 3/044
USPC ....... 601/15–18, 46; 604/1–3, 903; 222/175; 224/148.1–148.7
See application file for complete search history.

(56) References Cited

U.S. PATENT DOCUMENTS

| | | | |
|---|---|---|---|
| 4,903,864 A * | 2/1990 | Sirhan | A63H 37/00 2/160 |
| 5,468,218 A | 11/1995 | Ward | |
| 5,715,533 A * | 2/1998 | Stein | A42C 5/04 2/209.13 |
| 7,981,095 B2 * | 7/2011 | Grenon | A61H 7/00 604/289 |
| 8,142,373 B1 * | 3/2012 | Riles | A61H 23/02 601/48 |
| 8,758,279 B2 * | 6/2014 | Karnwie-Tuah | A61H 23/02 601/134 |
| 9,636,272 B2 * | 5/2017 | Yang | A61F 7/0085 |
| 2004/0237969 A1 * | 12/2004 | Fuller | A61H 35/02 128/858 |
| 2015/0224019 A1 * | 8/2015 | Barbera | A61H 23/02 601/46 |
| 2018/0279877 A1 * | 10/2018 | Berdahl | A61B 5/6898 |

FOREIGN PATENT DOCUMENTS

| | | |
|---|---|---|
| CN | 103622817 A | 3/2014 |
| CN | 107095782 A | 8/2017 |
| CN | 109259997 A | 1/2019 |
| WO | 2017105930 A1 | 6/2017 |

OTHER PUBLICATIONS

Lin-na Liu, English translation of CN 107,095,782 A, Aug. 29, 2017 (Year: 2017).*
International Search Report from International Application No. PCT/CN2019/094991, dated Oct. 9, 2019.

* cited by examiner

HEADACHE THERAPEUTIC INSTRUMENT

TECHNICAL FIELD

The present invention relates to the technical field of health products and medical devices, and in particular to a novel headache therapeutic instrument.

BACKGROUND OF THE INVENTION

Migraine is the most common primary headache and mainly shows up paroxysmal moderate-severe throbbing pain clinically. This headache is usually one-sided and generally can last for 4 h to 72 h in accompanying with nausea and vomiting. Light and sound stimuluses or daily activities may increase the headache, and quiet environment and rest may relieve it. Migraine is a common chronic neurovascular disease and usually starts in the childhood and teen years, achieving the peak period in the youth and middle ages. It is a common disease for women, and the ratio of men to women is about 1:(2-3). The morbidity rate of people is 5%-10%, and the disease is usually genetic. The cause of this disease is unclear.

Frequent onset of the migraine may influence the daily routine of the patient. The most direct influence is the sleep. Thus, the life and the work of the patient may be seriously influenced. Moreover, the long-time migraine may cause personality changes; generally, the patient having the migraine for a long time may become irascible, psychologically fragile and unconfident. Furthermore, the migraine also causes unfavorable influence to the human heart and cerebral vessels. Clinically, the headache attacks to usually cause cerebral therombosis, high blood pressure, and cerebral hemorrhage.

At present, there is not a special treatment method to eliminate the migraine. Usually the medicine oral administration or injection manner is used to relieve the pain, and physical manners such as massage, cold compress and the like are also used. However, although the effects of the medicine oral administration or injection are remarkable, the human body may generate drug dependence to a certain extent. Moreover, injection of the medicine needs a special appointed place, and the physical manner needs too long time to achieve the effect of relieving the headache.

Therefore, how to effectively relieve the migraine without the needing of the oral administration and injection of the medicine is a problem needing to be solved by a person skilled in the art.

SUMMARY OF THE INVENTION

The objective of the present invention is to propose a novel headache therapeutic instrument to solve problems in the prior art. Different from the traditional medicine taking and injecting manner, the novel headache therapeutic instrument of the present invention utilizes a transdermal treatment manner. Medicines permeate into human acupoints through the skin; thus, defects of oral administration and injection of the medicines are avoided. Additionally, massage is conducted in the medicine permeation process; thus, the migraine of a patient can be effectively relieved.

To achieve the above objective, the present invention provides the following solution:

The present invention provides a novel headache therapeutic instrument, comprising a wearable frame fitting for the human head, massage and transdermal medicine permeation devices, liquid medicine delivery tubes, a liquid medicine delivery device and a liquid medicine storage box.

The massage frame is provided with at least one acupoint locating hole corresponding to the human head. The massage and transdermal medicine permeation device is mounted on the massage frame and corresponds to the acupoint locating hole.

The liquid medicine delivery device delivers medicines in the liquid medicine storage box to the massage and transdermal medicine permeation devices through the liquid medicine delivery tubes. The massage and transdermal medicine permeation devices can conduct medicine permeation and massage on corresponding acupoints.

Preferably, the wearable frame comprises a transversely-arranged arc stripped head top supporting part matching with the head top and an annular stripped head fixing seat matching with the forehead. Mounting slots are formed in two sides of the head fixing seat. A locking seat is arranged on a side face of the mounting slot. Mounting pins are vertically arranged at two ends of the head top supporting part. The mounting pins are inserted into the mounting slots and penetrate through the locking seats to be fastened by a puller bolt.

Preferably, the back end of an annular body of the head fixing seat has an unclosed structure.

Preferably, the acupoint locating hole comprises an acupoint locating hole A corresponding to the Baihui and two acupoint locating holes B corresponding to the Taiyang on the two sides. The acupoint locating hole A is arranged at the top of the heat top supporting part. A mounting plane A is arranged at the top of a portion, corresponding to the acupoint locating hole A, of the head top supporting part. The mounting plane A is used for fixing the massage and transdermal medicine permeation device. The acupoint locating holes B are located on the two sides of the head fixing seat. A mounting plane B is arranged on the outer side of a portion, corresponding to each acupoint locating hole B, the head fixing seat. The mounting plane B is also used for fixing the massage and transdermal medicine permeation device.

Preferably, the massage and transdermal medicine permeation device comprises a liquid medicine delivery tube joint, a sponge body, a massage head, a motor and a housing. The inner side of the housing is fixedly connected with the mounting plane A or B.

The housing has a circular hood structure having a clamping hole at the central portion. The sponge body is cylindrical body. The inner side of the sponge body comes into contact with the human head sequentially through the clamping hole and the acupoint locating hole. The outer side of the sponge body is fixedly clamped with the clamping hole. The liquid medicine delivery tube joint is placed on a side wall of the housing and is communicated with the sponge body inserted into the inner side of the housing.

The motor is arranged on an outer end face of the housing. The massage head is connected with a rotary shaft of the motor. The motor drives the massage head to extrude the sponge body to massage the human head.

Preferably, the massage head is a triangular column with three chamfered angles. The rotary shaft of the motor is fixed connected with the massage head through two end faces of the massage head. The three chamfered angles of the massage head alternatively extrude the sponge body to massage the human head.

Preferably, the housing is fixedly connected or adhered with the mounting plane A or B through bolts.

Preferably, the head end of the head fixing seat is further provided with a mounting plane C. The liquid medicine delivery device is fixed to the mounting plane C. The liquid medicine storage box is fixed to the top of the liquid medicine delivery device.

The liquid medicine delivery device comprises a supporting shell fixed to the mounting plane C and three mini water pumps arranged in the supporting shell. The three mini water pumps are provided with feeding tubes communicated with the liquid medicine storage box and also provided with discharging joints. The discharging joints are respectively communicated with the three independently arranged liquid medicine delivery tubes, wherein two of the liquid medicine deliver tubes are respectively communicated with the liquid medicine delivery tube joints on the two sides of the head fixing seat, and the other is communicated with the liquid medicine delivery tube joint at the head top supporting part.

Preferably, the supporting shell is fixedly connected or adhered with the mounting plane C through bolts.

Preferably, the wearable frame is plastic, and a side in contact with the human head is adhered with one layer of silicone pad. A circuit tube for transmitting electric and electrical signals to the whole therapeutic instrument is arranged on the outer side of the wearable frame.

The present invention achieves the following technical effects compared with the prior art:

Different from the traditional medicine taking and injecting manner, the novel headache therapeutic instrument of the present invention utilizes a transdermal treatment manner. Medicines permeate into human acupoints through the skin; thus, defects of oral administration and injection of the medicines are avoided. Additionally, massage is conducted in the medicine permeation process under the combined action of the motor and the mini water pumps; thus, the migraine of a patient can be effectively relieved.

BRIEF DESCRIPTION OF THE DRAWINGS

To describe the technical solutions in the embodiments of the present invention or in the prior art more clearly, the following briefly introduces the accompanying drawings required for describing the embodiments. Apparently, the accompanying drawings in the following description show merely some embodiments of the present invention, and a person of ordinary skill in the art may still derive other accompanying drawings from these accompanying drawings without creative efforts.

Figure 1:
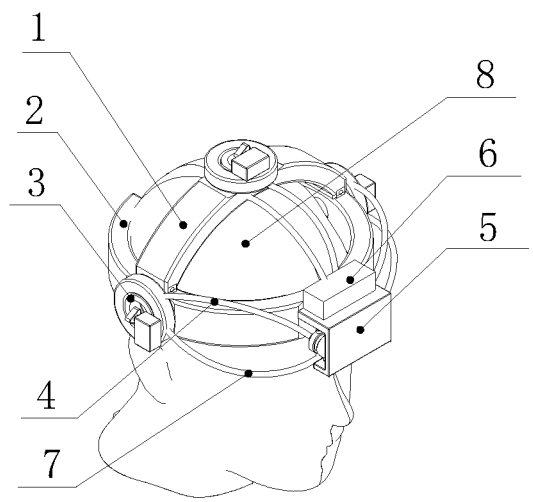
FIG. 1 is a schematic structural diagram of a novel headache therapeutic instrument in the present invention.

In the drawings: 1—head top supporting part, 11—mounting pin, 12—acupoint locating hole A, 13—mounting plane A, 2—head fixing seat, 21—mounting slot, 22—locking seat, 23—acupoint locating hole B, 24—mounting plane B, 25—mounting plane C, 3—massage and transdermal medicine permeation device, 31—liquid medicine delivery tube joint, 32—sponge body, 33—massage head, 34—motor, 35—housing, 4—liquid medicine delivery tube, 5—liquid medicine delivery device, 51—supporting shell, 52—mini water pump, 53—feeding tube, 54—discharging joint, 6—liquid medicine storage box, 7—circuit tube, and 8—human head.

DESCRIPTION OF THE PREFERRED EMBODIMENTS

The following clearly and completely describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

The objective of the present invention is to provide a novel headache therapeutic instrument to solve the problems in the prior art.

To make the foregoing objective, features, and advantages of the present invention more apparent and more comprehensible, the present invention is further described in detail below with reference to the accompanying drawings and specific embodiments.

Figure 2:
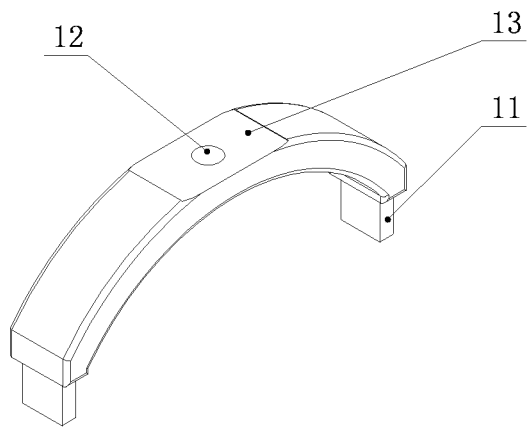
FIG. 2 is a schematic structural diagram of a head top supporting part in the present invention.
Figure 3:
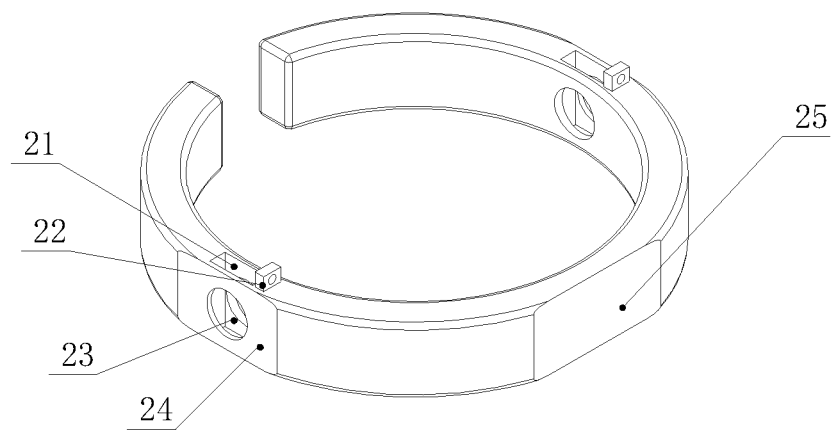
FIG. 3 is a schematic structural diagram of a head fixing seat in the present invention.

The present invention provides a novel headache therapeutic instrument, as shown in FIG. 1 to FIG. 3, comprising a wearable frame fitting for the human head 8, massage and transdermal medicine permeation devices 3, liquid medicine delivery tubes 4, a liquid medicine delivery device 5 and a liquid medicine storage box 6.

The massage frame is provided with at least one acupoint locating hole corresponding to the human head 8. The massage and transdermal medicine permeation device 3 is mounted on the massage frame and corresponds to the acupoint locating hole.

The liquid medicine delivery device 5 delivers medicines in the liquid medicine storage box 6 to the massage and transdermal medicine permeation devices 3 through the liquid medicine delivery tubes 4. The massage and transdermal medicine permeation devices 3 can conduct medicine permeation and massage on corresponding acupoints.

In the embodiment, the wearable frame specifically comprises a transversely-arranged arc stripped head top supporting part 1 matching with the head top and an annular stripped head fixing seat 2 matching with the forehead. Mounting slots 21 are formed in two sides of the head fixing seat 2. A locking seat 22 is arranged on a side face of the mounting slot 21. Mounting pins 11 are vertically arranged at two ends of the head top supporting part 1. The mounting pins 11 are inserted into the mounting slots 21 and penetrate through the locking seats 22 to be fastened by a puller bolt. Additionally, the back end of an annular body of the head fixing seat 2 has an unclosed structure; that is, the head fixing seat 2 can be transversely expanded to match with the heads of different persons. Moreover, the insertion depth of the mounting pin 11 in the mounting slot 21 can be also adjusted in the wearing process. The desired insertion depth is adjusted according to the head, and the bolt passes through the locating hole in the locking seat 22 to lock the mounting pin.

Preferably, the wearable frame is plastic, and a side in contact with the human head 8 is adhered with one layer of silicone pad. Specifically, one layer of silicone pad is respectively adhered on the inner sides of the head top supporting part and the head fixing seat of the wearable frame to improve the wearing comfortableness of the whole instrument and prevent the instrument from hurting the human head 8.

The headache therapeutic instrument of the present invention mainly aims to conduct medicine permeation and massage on the Baihui at the head top and the Taiyang on the two sides. Therefore, in the embodiment, the acupoint locating holes comprise an acupoint locating hole A 12 corresponding to the Baihui and acupoint locating holes B 23 corresponding to the Taiyang on the two sides.

The acupoint locating hole A 12 is arranged at the top of the heat top supporting part 1. A mounting plane A 13 is arranged at the top of a portion, corresponding to the acupoint locating hole A 12, of the head top supporting part. The mounting plane A 13 is used for fixing the massage and transdermal medicine permeation device 3. The acupoint locating holes B 23 are located on the two sides of the head fixing seat 2. A mounting plane B 23 is arranged on the outer side of a portion, corresponding to each acupoint locating hole B 24, the head fixing seat 2. The mounting plane B 24 is also used for fixing the massage and transdermal medicine permeation device 3.

Figure 4:
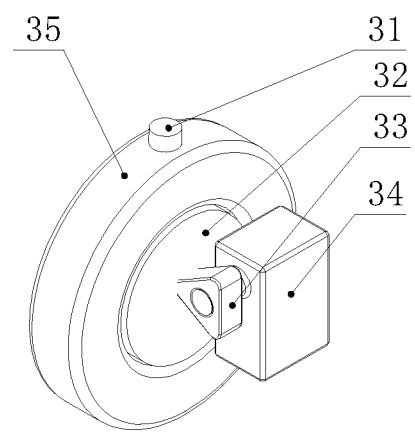
FIG. 4 is a schematic structural diagram of a massage and transdermal medicine permeation device in the present invention.

As shown in FIG. 4, in the embodiment, the massage and transdermal medicine permeation device 3 comprises a liquid medicine delivery tube joint 31, a sponge body 32, a massage head 33, a motor 34 and a housing 35. The inner side of the housing is fixedly connected with the mounting plane A 13 or B 24.

The housing 35 has a circular hood structure having a clamping hole at the central portion. The sponge body 32 is cylindrical body. The inner side of the sponge body 32 comes into contact with the human head 8 sequentially through the clamping hole and the acupoint locating hole. The outer side of the sponge body 32 is fixedly clamped with the clamping hole. The liquid medicine delivery tube joint 31 is placed on a side wall of the housing 35 and is communicated with the sponge body 32 inserted into the inner side of the housing.

The motor 34 is arranged on an outer end face of the housing 35. The massage head 33 is connected with a rotary shaft of the motor 34. The motor 34 drives the massage head 33 to extrude the sponge body 32 to massage the human head 8.

The massage head 33 is a triangular column with three chamfered angles. The rotary shaft of the motor 34 is fixed connected with the massage head 33 through two end faces of the massage head 33. The three chamfered angles of the massage head 33 alternatively extrudes the sponge body 32 to massage the human head 8.

In the embodiment, the housing 35 of the massage and transdermal medicine permeation device 3 is fixedly connected or adhered with the mounting plane A 13 or B 24 through bolts to fix the massage and transdermal medicine permeation device 3 to the head top supporting part 1 or the head fixing seat 2.

In the embodiment, the head end of the head fixing seat 2 is further provided with a mounting plane C 25. The liquid medicine delivery device 5 is fixed to the mounting plane C 25. The liquid medicine storage box 6 is fixed to the top of the liquid medicine delivery device 5.

Figure 5:
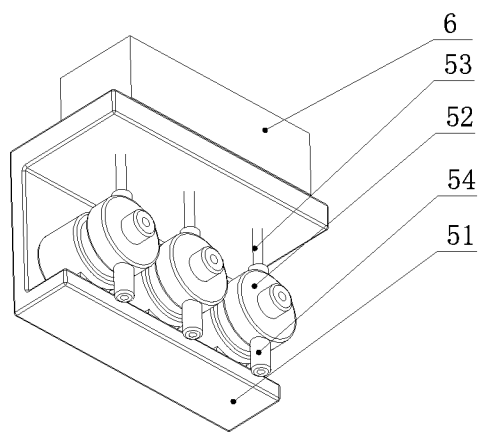
FIG. 5 is a schematic structural diagram of a liquid medicine delivery device in the present invention.

As shown in FIG. 5, the liquid medicine delivery device 5 comprises a supporting shell 51 fixed to the mounting plane C 25 and three mini water pumps 52 arranged in the supporting shell 51. The three mini water pumps 52 are provided with feeding tubes 53 communicated with the liquid medicine storage box 6 and also provided with discharging joints 54. The discharging joints 54 are respectively communicated with the three independently arranged liquid medicine delivery tubes 4, wherein two of the liquid medicine deliver tubes 4 are respectively communicated with the liquid medicine delivery tube joints 31 on the two sides of the head fixing seat 2, and the other is communicated with the liquid medicine delivery tube joint 31 at the head top supporting part.

In the embodiment, the liquid medicine delivery device 5 is fixedly connected or adhered with the mounting plane C 25 through the supporting shell 51.

Furthermore, in the embodiment, a circuit tube 7 for transmitting electric and electrical signals to the whole therapeutic instrument is arranged on the outer side of the wearable frame. One end of the circuit tube 7 is connected with a control and driving circuit of the therapeutic instrument, and the other end is respectively connected with the motor 34 and the mini water pumps 52 to provide electric and control signals for the motor 34 and the mini water pumps 52.

The working principle of the novel headache therapeutic instrument of the present invention is as follows: the therapeutic instrument utilizes the mini water pumps 52 to pump the liquid medicine to different acupoints, and stores the liquid medicine by utilizing the water storage characteristic of the sponge body 32; then, the motor 34 drives the massage heads 33 to extrude the sponge bodies to simultaneously achieve the effects of massage and transdermal permeation; thus, the physical treatment and medicine permeation treatment for the migraine are achieved.

Several examples are used for illustration of the principles and implementation methods of the present invention. The description of the embodiments is merely used to help illustrate the method and its core principles of the present invention. In addition, a person of ordinary skill in the art can make various modifications in terms of specific embodiments and scope of application in accordance with the teachings of the present invention. In conclusion, the content of this specification shall not be construed as a limitation to the present invention.

What is claimed is:
1. A headache therapeutic instrument, comprising a wearable frame adapted to fit on a human head, massage and transdermal medicine permeation devices, liquid medicine delivery tubes, a liquid medicine delivery device and a liquid medicine storage box, wherein the wearable frame is provided with at least one acupoint locating hole adapted to correspond to acupoints along the human head; the massage and transdermal medicine permeation devices are mounted on the wearable frame and correspond to the acupoint locating hole;

the liquid medicine delivery device delivers medicines in the liquid medicine storage box to the massage and transdermal medicine permeation devices through the liquid medicine delivery tubes; the massage and transdermal medicine permeation devices are capable of conducting medicine permeation and massaging on corresponding acupoints; and the wearable frame comprises a transversely-arranged arc stripped head top supporting part adapted to match with a top of the human head and an annular stripped head fixing seat adapted to match with the forehead; mounting slots are formed in both sides of the head fixing seat; locking seats are arranged on side faces of the mounting slots; mounting pins are vertically arranged at both ends of the head top supporting part; and the mounting pins a are inserted into the mounting slots and penetrate through the locking seats to be fastened and fixed by a puller bolt.

2. The headache therapeutic instrument according to claim 1, wherein a back end of an annular body of the head fixing seat has an unclosed structure.

3. The novel headache therapeutic instrument according to claim 1, wherein the at least one acupoint locating hole comprises an acupoint locating hole (A) corresponding to a Baihui acupoint and acupoint locating holes (B), corresponding to two Taiyang acupoints on both sides of the human head; the acupoint locating hole (A) is arranged at a top of the head top supporting part; a mounting plane (A) is arranged at the top, corresponding to the acupoint locating hole (A), of the head top supporting part; the mounting plane (A) is used for fixing one of the massage and transdermal medicine permeation devices; the acupoint locating holes B are located on the both sides of the head fixing seat; mounting planes (B) are arranged on an outer side, corresponding to the acupoint locating holes (B), of the head fixing seat; and each of the mounting planes (B) are also used for fixing each of the massage and transdermal medicine permeation devices.

4. The headache therapeutic instrument according to claim 3, wherein
   each of the massage and transdermal medicine permeation devices comprises a liquid medicine delivery tube joint, a sponge body, a massage head, a motor and a housing; an inner side of the housing is fixedly connected with the mounting plane (A) or (B);
   the housing has a circular hood structure having a clamping hole at a central portion; the sponge body is cylindrical; the inner side of the sponge body comes into contact with the human head sequentially through the clamping hole and the acupoint locating hole; an outer side of the sponge body is fixedly clamped with the clamping hole; the liquid medicine delivery tube joint is placed on a side wall of the housing and is in communication with the sponge body inserted into the inner side of the housing; and
   the motor is arranged on an outer end face of the housing; the massage head is connected with a rotary shaft of the motor; the motor drives the massage head to extrude the sponge body to massage the human head.

5. The headache therapeutic instrument according to claim 4, wherein the massage head is a triangular column with three chamfered angles; the rotary shaft of the motor is fixedly connected with the massage head through two end faces of the massage head; the three chamfered angles of the massage head alternatively extrude the sponge body to massage the human head.

6. The headache therapeutic instrument according to claim 5, wherein the housing is fixedly connected or adhered with the mounting plane (A) or (B) through bolts.

7. The headache therapeutic instrument according to claim 6, wherein
   a head end of the head fixing seat is further provided with a mounting plane (C); the liquid medicine delivery device is fixed to the mounting plane (C); the liquid medicine storage box is fixed to a top of the liquid medicine delivery device; and
   the liquid medicine delivery device comprises a supporting shell fixed to the mounting plane (C) and three mini water pumps arranged in the supporting shell; the three mini water pumps are provided with feeding tubes that are in communication with the liquid medicine storage box and also provided with discharging joints; wherein the liquid medicine delivery tubes comprise three independently arranged liquid medicine delivery tubes; the discharging joints joints are respectively in communication with three independently arranged liquid medicine delivery tubes, wherein two of the liquid medicine delivery tubes of the three independently arranged liquid medicine delivery tubes are respectively in communication with the liquid medicine delivery tube joints on the both sides of the head fixing seat, and a third liquid medicine delivery tube of the three independently arranged liquid medicine delivery tubes is in communication with the liquid medicine delivery tube joint at the head top supporting part.

8. The headache therapeutic instrument according to claim 7, wherein the supporting shell is fixedly connected or adhered with the mounting plane (C) through bolts.

9. The headache therapeutic instrument according to claim 1, wherein the wearable frame is plastic, and a side in contact with the human head is adhered with one layer of silicone padding; a circuit tube for transmitting electric and electrical signals to the headache therapeutic instrument is arranged on an outer side of the wearable frame.

* * * * *